United States Patent
Avila et al.

(10) Patent No.: US 7,074,424 B2
(45) Date of Patent: Jul. 11, 2006

(54) POLYALKYLENE GLYCOL VISCOSITY-ENHANCING POLYMERIC FORMULATIONS

(75) Inventors: Luis Z. Avila, Arlington, MA (US); Peter K. Jarrett, Sudbury, MA (US); Hildegard M. Kramer, Westport, CT (US); C. Michael Philbrook, Boston, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/996,184

(22) Filed: Nov. 28, 2001

(65) Prior Publication Data

US 2002/0127196 A1 Sep. 12, 2002

Related U.S. Application Data

(60) Provisional application No. 60/253,477, filed on Nov. 28, 2000.

(51) Int. Cl.
*A61F 2/02* (2006.01)
*A61K 47/30* (2006.01)

(52) U.S. Cl. .................... 424/426; 514/772.3
(58) Field of Classification Search ............... 424/422, 424/423, 424, 425, 426, 484, 488, 78.08, 424/78.17, 486; 514/54, 57, 59, 60, 62, 772.3
See application file for complete search history.

(56) References Cited

U.S. PATENT DOCUMENTS

| | | | |
|---|---|---|---|
| 3,325,472 A | 6/1967 | Sackler | |
| 4,629,623 A | 12/1986 | Balazs et al. | |
| 5,068,225 A | 11/1991 | Pennell et al. | |
| 5,410,016 A | 4/1995 | Hubbell et al. | |
| 5,510,418 A | 4/1996 | Rhee et al. | |
| 6,017,301 A | 1/2000 | Schwartz et al. | |
| 6,034,140 A | 3/2000 | Schwartz et al. | |
| 6,083,524 A * | 7/2000 | Sawhney et al. | 424/426 |
| 6,121,341 A | 9/2000 | Sawhney et al. | |
| 6,123,667 A * | 9/2000 | Poff et al. | 600/201 |
| 6,133,325 A | 10/2000 | Schwartz et al. | |
| 6,177,095 B1 * | 1/2001 | Sawhney et al. | 424/426 |
| 6,288,043 B1 * | 9/2001 | Spiro et al. | 514/54 |
| 6,685,883 B1 | 2/2004 | Taupin et al. | |

FOREIGN PATENT DOCUMENTS

EP 0 138 572 4/1985

(Continued)

OTHER PUBLICATIONS

Elisseeff, et al., "Photoencapsulation of chondrocytes in poly(ethylene oxide)-based semi-interpenetrating networks", J. Biomed. Mater. Res., vol. 51 (2), pp. 164-171 (Aug. 2000).

(Continued)

*Primary Examiner*—Carlos A. Azpuru
(74) *Attorney, Agent, or Firm*—Isabelle A. S. Blundell (57) ABSTRACT

Hyaluronic acid and polyalkylene glycol (PAG) based materials have been found to exhibit a synergistic interaction, in which the viscosity of the mixture is more than twice as high as the viscosity expected from the viscosity of the individual components. The mixture otherwise has similar properties to those of its constituents, and in particular will crosslink to form covalently crosslinked gels if the PEG carries crosslinkable groups. The viscous formulation adheres well to tissue, and has applications as a tissue sealant and in tissue coating, prevention of adhesions, cell immobilization, regeneration of cartilage, bone and other tissue, as well as in controlled delivery of hyaluronic acid to sites in the body. Related materials exhibit similar effects.

23 Claims, 9 Drawing Sheets

FOREIGN PATENT DOCUMENTS

EP   0 466 300   1/1992
WO   WO 01/00246   1/2001

OTHER PUBLICATIONS

Smeds et al., "Photocrosslinkable polysaccharides for *in situ* hydrogel formation", J. Biomed. Mater. Res., vol. 54, pp. 115-121 (2001).

Elisseeff, et al., "Photoencapsulation of chondrocytes in poly(ethylene oxide)-based semi-interpenetrating networks", J. Biomed. Mater. Res., vol. 51 (2), pp. 164-171 (Aug. 2000).

Smeds et al., "Photocrosslinkable polysaccharides for *in situ* hydrogel formation", J. Biomed. Mater. Res., vol. 54, pp. 115-121 (2001).

* cited by examiner

POLYALKYLENE GLYCOL VISCOSITY-ENHANCING POLYMERIC FORMULATIONS

CROSS-REFERENCE TO RELATED APPLICATIONS

This application claims priority to U.S. Provisional Application No. 60/253,477, filed Nov. 28, 2000.

BACKGROUND OF THE INVENTION

This application is generally in the field of polymeric materials for use in medicine, and more particularly relates to polyalkylene glycol-hyaluronic acid formulations. Throughout this application, various publications are referenced. The disclosures of those publications are hereby incorporated by reference into this application in their entireties.

Tailored biocompatible materials are widely used in medicine. These materials may be used to seal tissue after surgery, coat tissue to prevent adhesions, adhere tissue to tissue, stimulate regeneration of cartilage, bone and other tissue, and provide local bulking or a substrate for cell growth through implantation into sites in the body. These materials may also be used to deliver drugs, locally or systemically, to deliver cells to particular sites in the body, or to protect cells from attack by the immune system.

An important class of materials useful in for these types of applications is the polysaccharide, hyaluronic acid (HA), and its salts and derivatives. HA is found in the body serving in a variety of functions. The tissue adherence of unmodified HA is not strong. HA can be formed into a gel in the presence of trivalent ions and can be cross-linked to form gels of varying viscosity.

Reactive macromers, particularly of polyethylene glycol (PEG) and related polyalkylene glycols (PAGs), can be used to form gels. These gels also have some drawbacks. For instance, PAGs require a minimum concentration to form gels, typically several percent but preferably higher. The PAGs also have a tendency to swell after polymerization. They are often highly water-soluble. It is frequently difficult to achieve a sufficiently high viscosity in PAG solutions that the solution stays in place during polymerization. PAG solutions also typically have relatively small pores, which do not facilitate cell entry in tissue engineering applications.

Therefore PAGs have been mixed with other polymers to form a solution with the necessary properties to form the desired gels. Many water-soluble polymers are incompatible with PAGs and separate to form two or more phases in aqueous solutions. The best known of these phase-separating pairs are mixtures of PEG with dextran and with other polymers. Only a few polymers are known to interact, in the absence of specific group interactions (as distinguished from nonspecific bonding by hydrogen bonds and the like) or having opposite charges. These include PEG and polyacrylic acid, but the complex is reportedly formed only at low pH (e.g. pH 3–4) where some of the acrylate carboxyls are protonated. Thus, on mixing polymers it is expected that either no interaction or phase separation will occur.

HA and certain other polymers, herein referred to as "PAG-interacting polymers" ("PIPs"), exhibit an interaction with PAGs and PAG-based reactive macromers, producing a solution with a very high viscosity when mixed together. This result is described in U.S. Pat. No. 4,629,623 to Balazs et al. U.S. Pat. No. 4,629,623 discloses that high molecular weight hyaluronic salts and water soluble poly(ethylene oxides) form viscoelastic compositions which can be used in cosmetic formulations.

U.S. Pat. Nos. 6,017,301, 6,034,140, and 6,133,325 to Schwartz et al. teach forming bioadhesive, bioresorbable, anti-adhesion compositions from carboxyl-containing polysaccharides, such as carboxymethylcellulose (CMC), and polyethers, such as polyethyleneoxide (PEO). Schwartz teaches that compositions with the desired properties can be formed at a pH between 3 and 5 due to an association complex forming between the carboxyl containing polysaccharide and the polyether. The compositions are either dried and then applied to the body, or applied to the body in the liquid form.

It is therefore an object of the present invention to provide polymeric mixtures with an increased viscosity.

It is a further object of the present invention to provide methods for administering to a site in a patient a liquid which forms a bioadhesive, flexible gel at the site of administration.

It is a further object of the invention to deliver bioactive compounds to a patient through the application of viscous solutions which form gels.

SUMMARY OF THE INVENTION

A composition is formed of a mixture of a PAG-based macromer and HA or another material that increases the viscosity of the resulting mixture, as compared with the viscosity of the starting materials. The mixture may also demonstrate an increase in the pseudoplasticity (shear thinning), as compared to that present in the precursors. The mixture otherwise has similar properties to those of its constituents, and in particular will crosslink to form covalently crosslinked gels if the reactive macromer or PIP carries crosslinkable groups.

The viscous formulation adheres well to tissue, and can be used in applications as a tissue sealant and in tissue coating, prevention of adhesions, cell immobilization, regeneration of cartilage, bone and other tissue, as well as in controlled delivery of hyaluronic acid to sites in the body.

The composition may be applied to the body in a liquid form which gels in vivo to form a biocompatible, bioadhesive, flexible gel. Polymerization may occur either before or after applying the mixture to tissue, but preferably occurs after application. The gel may be used for the controlled delivery of HA or another material that increases the viscosity of the mixture. The release of HA may form spaces for cell growth and allow for the regeneration of cartilage, bone or other tissue at the site where the gel is applied. The composition may further contain cells and be used to immobilize the cells in the resulting gel.

The composition may form a stabilized depot in the patient to provide lubricity to a tissue. Formation of crosslinked low-concentration HA/PAG mixtures in situ provides a material having low tensile strength and very high elastic compliance (ease of stretching). It is a suitable material for several medical purposes, including treatment of joints, and of other sites requiring lubrication, and may also be useful in ocular applications, particularly replacement of vitreous humor.

BRIEF DESCRIPTION OF THE DRAWINGS

FIG. 1 is a graph of stirring rate (i.e. rate of shear) (RPM) versus apparent viscosity (cP) at constant temperature (25°

C.) for a solution containing 5% 20 KTLA (as defined in the examples) and 0.25% HA and control solutions.

DETAILED DESCRIPTION OF THE INVENTION

Compositions

The compositions contain a reactive macromer and a PAG-interacting polymer (PIP), i.e. a polymer which when mixed with the reactive macromer results in a solution with an increased viscosity, as compared with the precursors. The reactive macromer is typically a PAG or PAG-based macromer. The PIP is typically a glycosaminoglycan (GAG), such as HA.

The mixtures are polymerized prior to or after application to a patient to form a hydrogel.

Reactive Macromers

In the preferred embodiment, one component of the gel-forming solution is a reactive macromer. The reactive macromer is a macromer which reacts, spontaneously or under the influence of light, heat or other activating conditions or reagents, to form a covalently crosslinked polymeric structure. In the preferred embodiment it is a polyalkylene glycol (PAG) or PAG-based macromer.

The PAG may be a homopolymer or copolymer comprising at least about 50% by weight of alkylene glycol subunits, particularly ethylene glycol and propylene glycol. Suitable PAGs include polyethylene glycol (PEG) and copolymers of ethylene glycol with propylene glycol (poloxamers, meroxapols; e.g., PLURONIC® surfactants.)

In the preferred embodiment, the PIP/reactive macromer mixture is crosslinked. Preferably, the reactive macromer is a covalently-crosslinking PAG which has a biodegradable linking group between the crosslinking group (e.g., an acrylate, or other reactive group such as a succinimidate, isocyanate, etc.) and the backbone polymer. Polymers of this sort, with PEG backbones and various crosslinking groups, as well as reactively-derivatized HA and other materials, are described in U.S. Pat. No. 5,410,016 to Hubbell, et al. In all of the examples, except for Example 8, the PAG macromers are derivatized to contain chemically-reactive groups. These groups are typically ethylenically-unsaturated groups, such as acrylate groups. Generally, the PAG is covalently crosslinked, while the PIP is not crosslinked to the PAG gel structure (although it may be partially or completely immobilized by entrapment in the structure). Alternatively, the PIP may crosslink, and thereby immobilize a PAG. If the PIP is crosslinkable, it preferably contains a biodegradable group between the crosslinkable group (e.g., an acrylate, or other reactive group such as a succinimidate and isocyanate) and the PIP.

The PAG materials in the following examples include two types of reactive PEGs, non-derivatized PEGs (with a molecular weight of 35 kDa), and PLURONIC® F-127, which is a poloxamer (i.e. polyethylene glycol—polypropylene glycol copolymer with a molecular weight of approximately 12.6 kDa). The reactive materials are based on PEG molecules with a molecular weight of 20 or 35 kDa. Some of the active PEGs may be linked together to form dimeric and trimeric species. The reactive PEGs typically contain degradable end groups, and are capped by reactive species. In the examples, the reactive PEGs typically contain acrylate groups, though other reactive groups could be present. Generally, useful PAGs contain a molecular weight of less than 100 kDa, such as 12 kDa. If a non-degradable gel were required for an application, then a PAG with covalently-bound reactive groups, but without interposed degradable linkages, would provide the required effect.

PAG-Interacting Polymers

Several polymers have been found to be effective as PIPs in conjunction with a PAG-based component. A PIP exhibits an increase in viscosity when mixed with the above-described reactive macromers or imparts pseudoplasticity to a solution containing a reactive macromer. Polymers which act with PAGs to increase the viscosity of the resulting mixture include: glycosaminoglycans (GAG), such as hyaluronic acid (HA), carboxymethyl cellulose (CMC), dextran, dextran sulfate, and polyvinylpyrrolidone (PVP).

The GAGs include polymers derived from a GAG by partial hydrolysis and/or covalent derivatization with small organic molecules, and typically contain molecular weights less than about 3 kDa. HA is a glycosaminoglycan that is composed of glucuronic acid and N-acetylglucosamine. Among hyaluronic acid preparations, the increase in viscosity is significantly decreased for HAs below 500 kDa, although it is still observable in HAs with molecular weights of 150 kDa.

The mixtures may contain from 0.1% to 20% PIP. Preferably, the mixtures contain 0.5 to 5% PIP. The reactive macromer content may range from 2 to 30%. In the preferred embodiment the mixture contains 4% to 20% PAG or PAG-based macromer and 0.2–5% PIP.

Crosslinking Groups

In the preferred embodiment, the reactive macromer contains ethylenically unsaturated reactive groups. These groups are preferred due to their excellent stability in solution and low reactivity with typical PIPS. Further, when the reactive macromer contains ethylenically unsaturated reactive groups, external energy sources, such as light (photopolymerization) or heat, can be used to form the hydrogel.

This use of an external energy source allows for excellent control of the polymerization reaction.

Other reaction chemistries can also be used, particularly when devices are produced ex vivo for subsequent in vivo application. Suitable reactive groups include isocyanate and isothiocyanate groups, for reaction with amines or alcohols or thiols. The reaction of these groups is preferably directed away from the PIP, particularly if the PIP is a polysaccharide, by providing small molecule or macromeric groups of high reactivity in such reactions, such as primary amines and thiols. Less reactive leaving groups can be used in such reactions, including succinimidates, carbonyl imidazoles, and other reactive groups of similar properties known in the art. These reactive groups are particularly preferred when the reaction is to be conducted in an aqueous solution.

Crosslinking can also be performed with oxirane-containing groups and cyclic imines, although these groups may be prone to react with the PIP. Cyclic maleimides, preferably attached to the reactive macromers, are ethylenically unsaturated, but can react, even in the absence of free radicals, with thiols or amine groups.

At least some of the macromers or small molecules need to be at least bifunctional to support gel formation from molecules during a free-radical reaction. With polyurethane formation or in other reactions using leaving groups, it is necessary to have a predominance of bifunctional molecules, and at least some molecules that are trifunctional or of higher functionality.

Ancillary Reagents

The PIP/reactive macromer mixtures and gels may contain any of the materials conventionally used in pharmaceutical formulations, including salts, buffers, osmotic stabilizers, nutritive ingredients for cells, excipients, surfactants, antibiotics and other preservatives, and antioxidants to protect the polymeric materials. The PIP/reactive macromer mixtures and gels may also contain materials inhibiting polymerization in storage, such as quinones for ethylenically unsaturated materials. Further, the PIP/reactive macromer mixtures and gels may contain materials that stimulate or initiate polymerization, including initiators, photoinitiators, electron transfer reagents, enzymes, small molecule co-monomers to facilitate polymerization (e.g. ethylenically unsaturated monomers), and oxidants. Any of the above-mentioned materials may be bound or otherwise attached to the reactive macromers. Materials which spontaneously polymerize, stimulate polymerization, or are otherwise incompatible with the mixture during long-term storage may be stored as separate solutions and mixed with the PIP/reactive macromer mixture just before or during application.

Properties of the PIP/Reactive Macromer Mixtures

A highly viscous state is obtained by mixing a PIP with a reactive macromer. This increase in viscosity demonstrates that some form of interaction occurs between the PIP and the reactive macromer.

The high viscosity has several benefits. It facilitates controlled deposition of these materials. It allows formation of crosslinked gels at lower concentrations of reactive macromer than would otherwise be possible. In turn, these lower-concentration, more-porous gels are particularly effective for local delivery of PIPs or other materials, such as drugs, at a particular site. The gel formulations also are better able to remain in place during polymerization. Further, because of their lower macromer concentration, the resulting gels swell less. In addition, gelation of PIP/reactive macromer composites may reduce the susceptibility of PIPs, particularly natural PIPs, such as HA, to hydrolyzing enzymes (e.g., hyaluronidase). This extend the biological lifetime of the HA containing gel.

Figure 1:
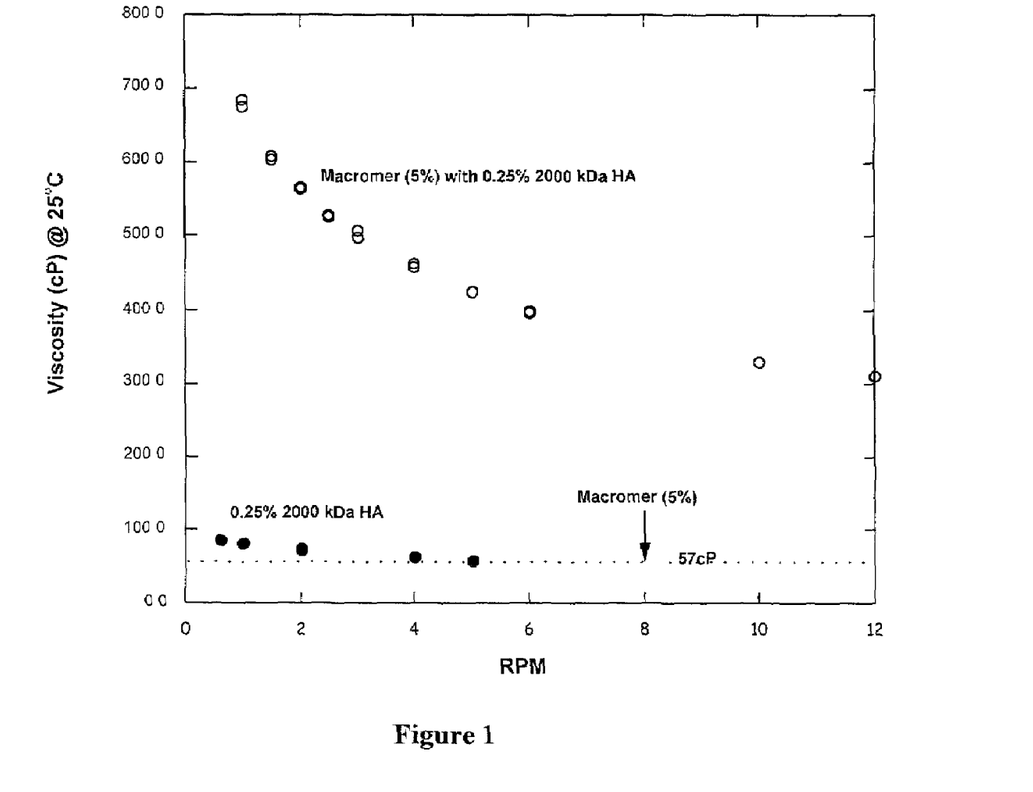
Figure 2:
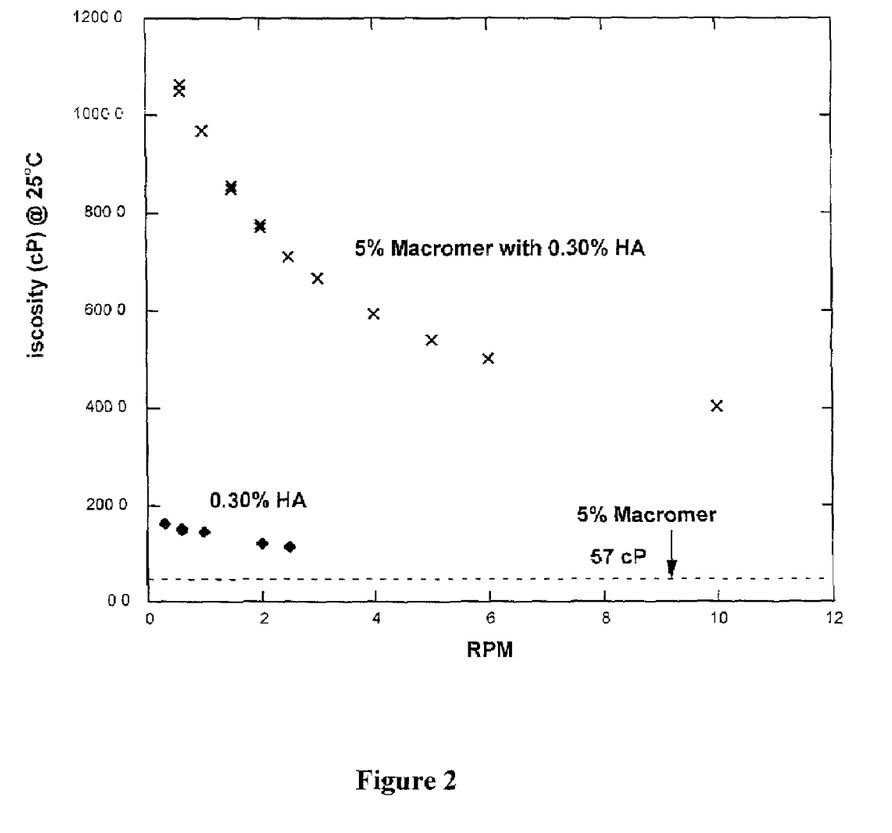
FIG. 2 is a graph of stirring rate (RPM) versus apparent viscosity (cP) at constant temperature (25° C.) for a solution containing 5% 20KTLA and 0.35% HA and control solutions.

Most mixtures of PIPs and reactive macromers, such as PAGs and PAG-based macromers, exhibit pseudoplasticity, also known as "shear thinning" (see e.g. FIGS. 1 and 2). Such materials are highly viscous at rest, but become less viscous under shear. Thus, these mixtures have the useful property of flowing readily during application and then spontaneously becoming highly viscous and thus relatively immobile after application to a site. This allows time for the materials to polymerize or be polymerized after application with minimal pre-polymerization migration of the materials. The effect can be observed at very low concentrations of PIP, such as 0.25% HA in macromer solution, and is believed to be present at even lower concentrations, including 0.1 or even 0.05%.

Methods of Making the PIP/Reactive Macromer Mixtures

The PIP may be added to a solution containing a reactive macromer, after mixing the solution, may be administered to a site in a patient and then polymerized in situ. Alternatively, the solution can be polymerized ex vivo and administered as a gel to the patient.

Polymerization

Polymerization may occur by any known method. For example, U.S. Pat. Nos. 6,121,341, 6,083,524, and 5,410,016, hereby incorporated by reference, each describe methods of polymerizing monomers to form hydrogels. In U.S. Pat. No. 5,410,016, application of biodegradable macromers to tissue, followed by photopolymerization to form a gel is described. Two methods for photopolymerizing gels are described. In "bulk" polymerization, a suitable photoinitiator and accessory reagents are solubilized or dispersed in a solution of gelling macromers. On application of light, the entire solution volume crosslinks to form a gel, which acts as a local barrier or drug depot. U.S. Pat. No. 6,121,341 describes a priming method. The priming method is suitable for any mode of polymerization, including photopolymerization and chemical or thermal polymerization. U.S. Pat. No. 6,083,524 describes the formation of water-soluble macromers, which include at least one hydrolyzable linkage, at least one water-soluble polymeric block, and at least one polymerizable group. The macromers are polymerized using free radical initiators under the influence of long wavelength ultraviolet light or visible light excitation.

Methods of Use

The PIP/reactive macromer hydrogels can be used in a number of medical and cosmetic applications. For example, the PIP/reactive macromer hydrogels can form tissue coatings and tissue sealants; deliver therapeutic substances; provide lubrication; fill spaces or provide tissue bulking; replace vitreous fluid; treat the retina, including the detached retina; prevent adhesions; adhere tissue to tissue or to a medical device; coat a medical device, such as an implant; embolize; encapsulate cells, tissues and organs; immobilize cells, tissue and organs; regenerate of cartilage, bone and other tissue; and be used to deliver oral medications.

Mixtures which contain a PIP can be used in sites where retention of the PIP may be useful. If HA is incorporated into a mixture with a reactive PAG macromer and polymerized, then the material can serve as a joint lubricant and can also optionally carry drugs for local delivery to the joint. It can also serve in applications for the prevention of adhesions.

In another aspect, the mixture is used to improve the retention of a drug depot for small ionic drugs. In this application, a PIP, which carries a charge, is mixed with the PAG-based macromer to form a matrix. If the matrix contains drugs with a charge that is opposite to the charge of the PIP, the efflux of drugs will be retarded. Similarly, drugs with an affinity for the PIP will also be retarded in their efflux from the gel.

In another aspect, the mixture may be applied to tissue to form a barrier on the tissue surface. In this application, the PAG-based macromer is polymerized in an aqueous solution containing a PIP and preferably a GAG, to form a barrier on tissue. The resulting barrier has a PIP exposed on at least part of its surface. The barrier may be formed on a tissue surface, or formed by polymerization and then applied to a surface. The barrier may be used for several medical purposes such as to prevent adhesions; to reduce friction between a tissue and another material, including tissue; and to locally deliver therapeutic materials, including polymeric therapeutics. The barrier may also be used to retain cells, tissue fragments or other particles at or within a site in the body.

In another aspect, the mixture is used to impart pseudoplasticity to a non-pseudoplastic PAG. In particular such the mixture may contain a low concentration of the PIP, such as 1% wt/vol. or less.

Methods of Application

The compositions containing a mixture of an PIP and a reactive macromer may be applied by any conventional means. These include delivery of solutions by pump, syringe, brush, spatula, or spray. A solution containing a mixture of the PIP and the reactive macromer may be made in situ, by stirring, brushing, rubbing or the like, or by spraying two or more solutions at the same site, or by mixing just before delivery to a site. In addition, the composition may be applied in non-liquid form by local reconstitution of dry or solid materials with bodily fluids or fluids applied to the site. The materials may be solids, dispersions or powders of the unpolymerized materials, or of the materials after polymerization.

Materials may be polymerized ex vivo and applied at a site as gels, or as dried or lyophilized gels, either in intact or particulate form, or as a coating on a device. Any application may further include medications, drugs, excipients, or other active or cosmetically-effective ingredients.

EXAMPLES

The present invention will be further understood by reference to the following non-limiting examples. In the examples, a PEG-based reactive macromer, referred to as 35KTLA, consists of PEG molecules with a molecular weight of 35 kDa, partially concatenated with trimethylene carbonate (TMC); end-capped with TMC (T) and lactide (L) units, typically several of each; and terminated with acrylate (A), a reactive group. The reactive macromer 20KTLA is similarly constructed, but consists of PEG molecules with a molecular weight of 20 kDa. The 35KTLA and 20KTLA macromers are biodegradable by virtue of their T and L groups; the ester bonds of which are well known to be hydrolytically unstable in the body. U.S. Pat. No. 6,083,524 describes the synthesis in detail.

Example 1

Viscosity and Modulus of 20KTLA and 35KTLA Solutions with and without 1% HA (500 kDa).

A 10 g aqueous formulation consisting of 1 g 20KTLA, 54 mg TEOA, 80 mg mono-potassium phosphate (KPhos), 40 mg vinylcaprolactam (VC), and 0.4 mg of Eosin-Y was prepared. To 5 g of this solution, 50 mg of 500 kDa sodium hyaluronate (HA) was added. Similarly, a 10 g aqueous formulation consisting of 2 g 35KTLA, 120 mg TEOA, 102 mg KPhos, 0.4 mg Eosin-Y, and 50 mg VC was prepared. To 5 g of this solution, 50 mg of 500 HA was added.

Table 1 summarizes the viscosities for each solution with and without HA. The viscosities of these solutions were obtained at 25° C. The moduli of the hydrogels, obtained after photopolymerization using visible light for 40, 80 or 180 seconds at 100 mW/cm$^2$, are also summarized in Table 1.

The viscosities of the formulations with 1% 500 kDa HA were significantly higher than the corresponding macromer formulations without the added HA. The moduli of the hydrogels are somewhat lower in the formulations containing 1% HA than in those without HA.

TABLE 1

Viscosity and Modulus with and without 1% HA (500 kDa)

| Material | HA content | Formulation Viscosity | Hydrogel Modulus |
|---|---|---|---|
| 20 KTLA | — | 5608 cP | 191 kPa (40 sec) |
| | | | 193 kPa (80 sec) |
| 20 KTLA | 1% | 12160 cP | 97 kPa (40 sec) |
| | | | 157 kPa (80 sec) |
| 35 KTLA | — | 1194 cP | 274 kPa (40 sec) |
| | | | 301 kPa (180 sec) |
| 35 KTLA | 1% | 3724 cP | 224 kPa (40 sec) |
| | | | 310 kPa (180 sec) |

Example 2

Gel Formation by Aqueous Solutions Containing 35KTLA and HA.

A first aqueous 5.028 g formulation was prepared containing 0.9005 g 35KTLA, 0.0302 g HA, 0.03 g ferrous gluconate (Fe-Gluconate), and 25 µL VC. A second aqueous 5.028 g formulation was prepared containing 0.9005 g 35KTLA, 0.0302 g HA, 126.3 ppm t-Butylperoxide, and 25 µL VC.

Five drops of the first solution were added to 5 drops of the second solution, and the mixture was rapidly mixed resulting in the formation of a hydrogel almost instantaneously (i.e., in less than 2 seconds). The rapid formation of a gel suggests that the presence of HA did not interfere with chemical initiation reaction between ferrous ion and hydroperoxide.

Example 3

Delivery of Aqueous Solutions Containing 35KTLA and HA.

The first aqueous solution described in Example 2 was loaded into one syringe and the second aqueous solution described in Example 2 was loaded into a second syringe. Both syringes were placed in a dual syringe holder. A device containing a 1 inch-long static mixer was attached to the end of the syringes. When the aqueous solutions were released from the syringes in a 1:1 ratio, the mixture gelled almost instantaneously.

Example 4

Effect of Change in Shear Rate on 20KTLA/HA Mixtures.

A 10 g aqueous formulation consisting of 1 g 20KTLA, 54 mg TEOA, 80 mg KPhos, 40 mg VC, and 0.4 mg of Eosin-Y was prepared. To 5 g of this solution 12.5 mg of 2000 kDa HA was added, and the mixture was thoroughly mixed. The resulting mixture contained 5% 20KTLA and 0.25% HA (wt/wt). To another 5 g of the above-described solution 15 mg of 2000 kDa HA was added, and the mixture was thoroughly mixed. The resulting mixture contained 5% 20KTLA and 0.30% HA (wt/wt).

Viscosity readings of these formulations were obtained by varying RPM at a constant temperature of 25° C. The results are shown in FIGS. 1 and 2.

FIG. 1 depicts the change in apparent viscosity (cP) for the mixture with 0.25% HA and the controls, 0.25% HA in aqueous solution, and 5% 20KTLA in aqueous solution, at increasing shear rates (RPM). The macromer, alone, exhibited a constant viscosity of 57 cP. For increasing shear rate, the viscosity of HA, alone, decreased slightly, from about 90 cP to 60 cP. In contrast, the viscosity for the mixture with 0.25% HA and 5% 20KTLA, which began at 695 cP (at 1.5 RPM), decreased exponentially for increasing shear rate to 310 cP (at 12 RPM).

FIG. 2 depicts the change in apparent viscosity (cP) for the mixture with 0.30% HA and the controls, 0.30% HA (alone) in aqueous solution and 5% 20KTLA (alone) in aqueous solution, at increasing shear rates (RPM). The 20KTLA (alone) exhibited a constant viscosity of 57 cP. For increasing shear rate, the viscosity of HA (alone) decreased slightly, from about 190 cP to 100 cP. In contrast, the viscosity for the mixture with 0.30% HA and 5% 20KTLA decreased exponentially for increasing shear rate, beginning at about 1,050 cP (at 1.5 RPM) and ending at about 400 cP (at 10 RPM).

The mixtures of 20KTLA and HA resulted in pseudoplastic solutions. This property is indicated by the dependence of the apparent viscosity on the shear rate.

Example 5

Effect of Change in Shear Rate on 20KTLA/PVP Mixtures.

A 10 g aqueous formulation consisting of 0.5 g 20KTLA, 0.5 g of polyvinylpyrrolidone (PVP) (MW 1,000 kDa), 50 mg TEOA, 80 mg KPhos, 40 mg VC, and 0.4 mg of eosin was prepared. The viscosity of the formulation was taken at various shear rates (RPM) at a constant temperature of 25° C. The results of the measurements for the above formulations and the controls are shown in FIG. 3.

Figure 3:
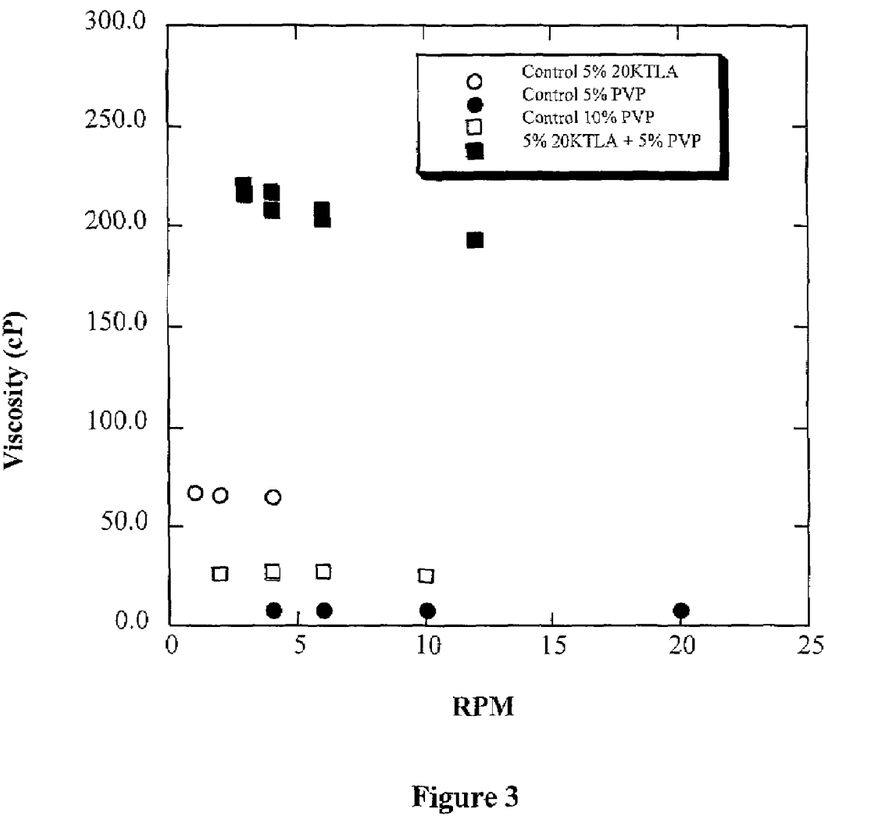
FIG. 3 is a graph of stirring rate (RPM) versus apparent viscosity (cP) at constant temperature (25° C.) for a solution containing 5% 20KTLA and 5% polyvinylpyrrolidone (PVP) and control solutions.

FIG. 3 depicts the change in apparent viscosity (cP) for the mixture of 5% 20KTLA and 5% PVP, 5% PVP (alone) in aqueous solution, 10% PVP (alone) in aqueous solution, and 5% 20KTLA (alone) in aqueous solution at increasing shear rates (RPM). The 5% 20KTLA (alone) solution exhibited a constant viscosity of about 57 cP. For increasing shear rate, the viscosity of PVP (alone) remained essentially constant, with 5% PVP (alone) at about 5 cP, while the viscosity of 10% PVP (alone) was higher, at about 25 cP. In contrast, the viscosity for the mixture 5% 20KTLA and 5% PVP decreased for increasing shear rate, beginning at about 225 cP (at 3 RPM) and ending at about 190 cP (at 12 RPM). The pseudoplasticity of the 20KTLA/PVP solution is indicated by the dependence of the apparent viscosity on the shear rate.

Example 6

Effect of Change in Shear Rate on 20KTLA/CMC Mixture.

A 10 g aqueous formulation consisting of 0.5 g 20KTLA, 0.1 g carboxymethylcellulose (CMC) (high viscosity, food grade), 50 mg TEOA, 80 mg KPhos, 40 mg VC, and 0.4 mg of eosin-Y was prepared. The viscosities of the formulation and control formulations were taken at various RPM at a constant temperature of 25° C. The results of the measurements for the above formulations and the controls are shown in FIG. 4.

Figure 4:
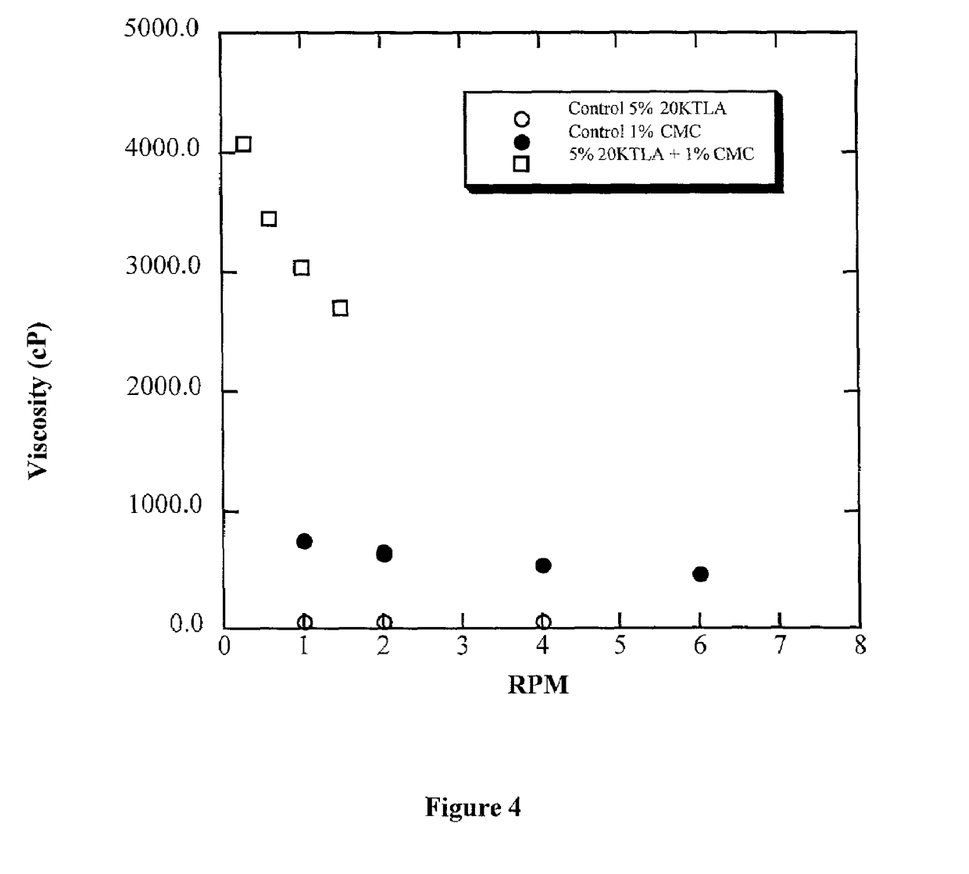
FIG. 4 is a graph of stirring rate (RPM) versus apparent viscosity (cP) at constant temperature (25° C.) for a solution containing 5% 20KTLA and 1% carboxymethylcellulose (CMC) and control solutions.

FIG. 4 depicts the change in apparent viscosity (cP) for the mixture of 5% 20KTLA and 1% PVP and controls, 1% CMC (alone) in aqueous solution and 5% 20KTLA (alone) in aqueous solution, at increasing shear rates (RPM). The 5% 20KTLA (alone) solution exhibited a constant viscosity of about 57 cP. For increasing shear rate, the viscosity of CMC (alone) decreased from about 750 cP (at 1 RPM) to about 400 cP (at 6 RPM). In contrast, the viscosity for the mixture 5% 20KTLA and 1% CMC decreased for increasing shear rate, beginning at about 4,100 cP (at 0.3 RPM) and ending at about 2,750 cP (at 1.5 RPM). The pseudoplasticity of the 20KTLA/CMC solution is indicated by the dependence of the apparent viscosity on the shear rate.

Example 7

Effect of HA Molecular Weight and Concentration on Modulus, Viscosity, and Equilibrium Swelling.

A 10 g aqueous formulation consisting of 1 g 20KTLA, 54 mg TEOA, 80 mg KPhos, 40 mg vinylcaprolactam (VC), 0.4 mg of Eosin-Y, and 8.826 g water was prepared. Sodium hyaluronate, with the molecular weights of 500 kDa, 1000 kDa and 2000 kDa, was added to aliquots of the above formulation to yield formulations containing 0.25%, 0.5%, 0.75% and 1.0% HA. The effect of molecular weight and concentration of HA on the viscosity of solutions and moduli of resulting gels are tabulated below in Table 2.

Figure 5:
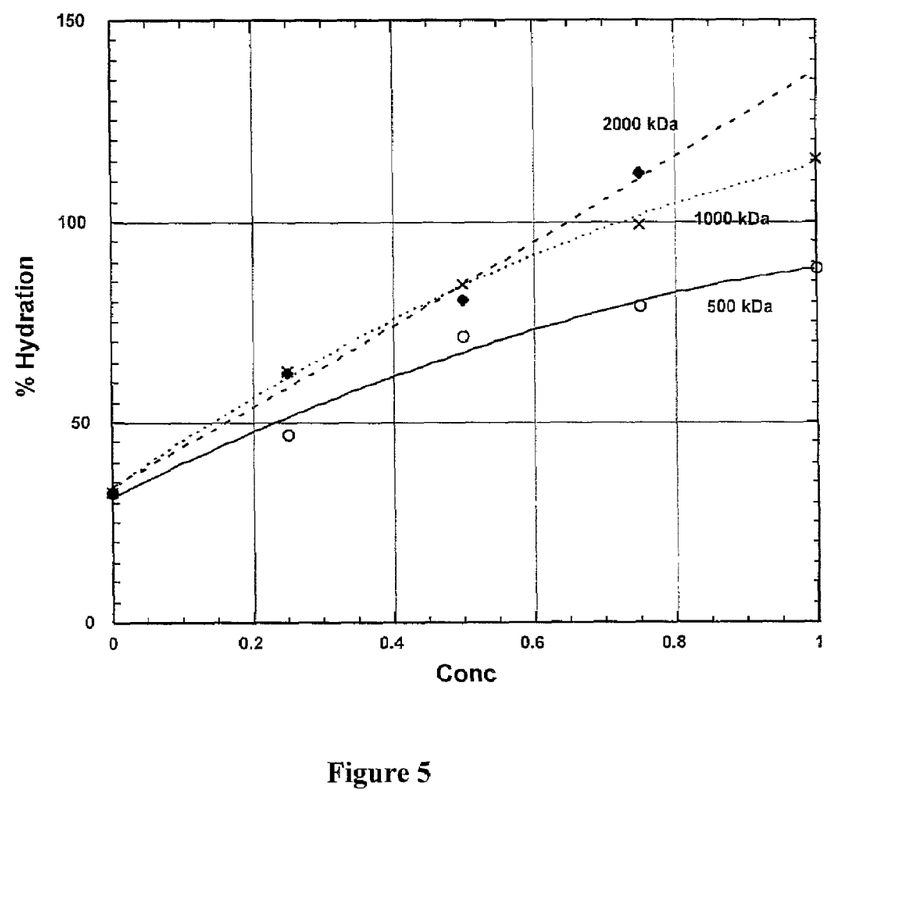
FIG. 5 is a graph of concentration of HA versus percent hydration (%) for solutions containing 20KTLA and HA at different molecular weights (500 kDa, 1000 kDa, and 2000 kDa) at a temperature of 37° C.

FIG. 5 shows the equilibrium swelling of these hydrogels in phosphate buffered saline (PBS) at 37° C. where equilibrium swelling is defined as the increase in the weight of the hydrogel due to uptake of water. Generally, as concentration and molecular weight increase, the weight of the hydrogel increases since it takes in more water.

TABLE 2

Effect of Molecular Weight and Concentration of HA on Viscosity and Modulus of 5% 20 KTLA.

| MW of HA | % HA | | | | |
|---|---|---|---|---|---|
| | 0.00% | 0.25% | 0.50% | 0.75% | 1.00% |
| | MODULUS (kPa) (40 sec illumination) | | | | |
| Control | 58 | | | | |
| 500 kDa | | 61 | 40 | 38 | 35 |
| 1000 kDa | | 41 | 41 | 39 | 37 |
| 2000 kDa | | 44 | 37 | 39 | |

TABLE 2-continued

Effect of Molecular Weight and Concentration of HA on Viscosity and Modulus of 5% 20 KTLA.

| MW of HA | % HA | | | | |
|---|---|---|---|---|---|
| | 0.00% | 0.25% | 0.50% | 0.75% | 1.00% |
| MODULUS (kPa) (80 sec illumination) | | | | | |
| Control | 66 | | | | |
| 500 kDa | | 59 | 55 | 54 | 52 |
| 1000 kDa | | 59 | 55 | 56 | 56 |
| 2000 kDa | | 44 | 57 | 53 | |
| VISCOSITY (cP) | | | | | |
| Control | 56.7(*) | | | | |
| 500 kDa | | 106.3(*) | 176.2(*) | 301.8 | 529.2 |
| 1000 kDa | | 195.3/274.7(*) | 721.6 | 3228 | 6696 |
| 2000 kDa | | 183.3/377.1 | 684.8 | 13890 | |

(*)viscosity taken with CP-40 spindle; otherwise with CP-50

Example 8

Effect of Shear Rate on PEG/HA Mixture.

Figure 6:
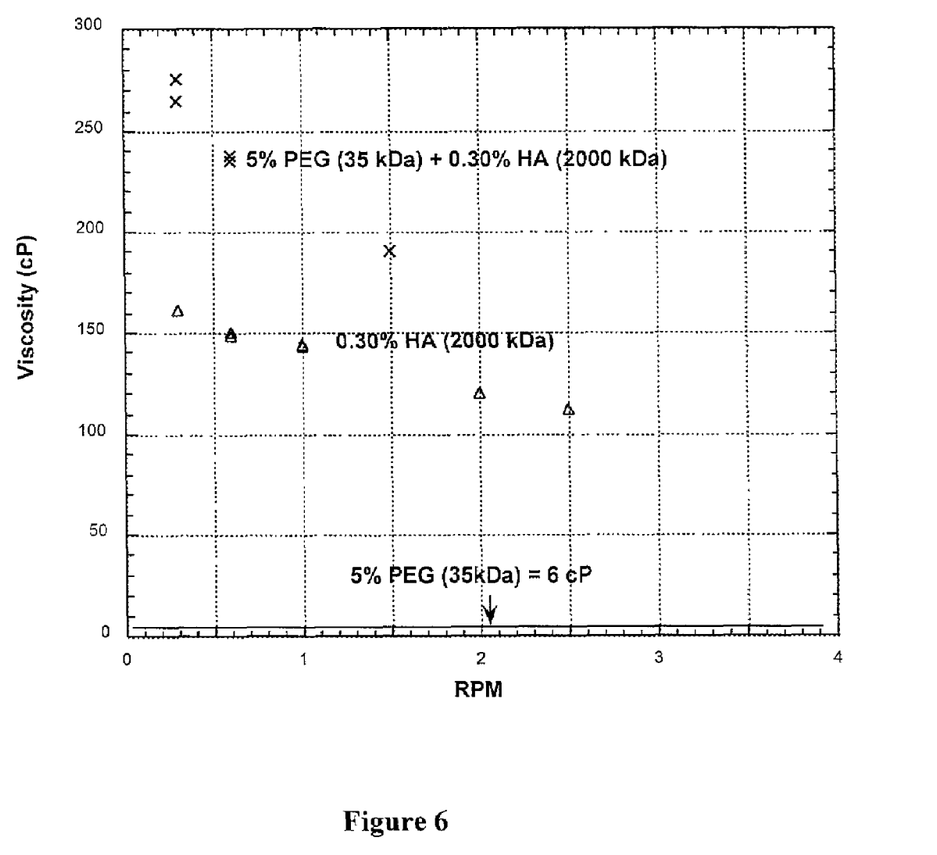
FIG. 6 is a graph of stirring rate (RPM) versus apparent viscosity (cP) at constant temperature (25° C.) for a solution containing 5% PEG (35 kDa) (i.e. non-derivatized PEG) and 0.30% HA (2000 kDa).

A 10 g aqueous formulation consisting of 0.5 g non-derivatized polyethylene glycol (PEG) with a molecular weight of 35 kDa, 30 mg HA with a molecular weight of 2000 kDa, 50 mg TEOA, 80 mg KPhos, 40 mg VC, and 0.4 mg of eosin-Y was prepared. The viscosities of the formulation and control formulations were taken at a variety of shear rates (RPM) at a constant temperature of 25 C. FIG. 6 graphically depicts the results of these measurements.

The 5% PEG (alone) solution exhibited a constant viscosity of 6 cP. For increasing shear rate, the viscosity of 0.30% HA (alone) decreased from about 160cP (at 0.3 RPM) to about 110 cP (at 2.5 RPM). In contrast, the viscosities for the mixture where much greater. The viscosity for the mixture 5% PEG and 0.30% HA decreased for increasing shear rate, beginning at about 275 cP (at 0.3 RPM) and ending at about 190 cP (at 1.5 RPM).

Example 9

Effect of Change in Shear Rate on 20KTLA/Dextran Mixture.

A 10 g aqueous formulation consisting of 0.5 g 20KTLA, 0.5 g dextran (with a molecular weight of 500 kDa), 50 mg TEOA, 80 mg KPhos, 40 mg VC, and 0.4 mg of eosin-Y was prepared. The viscosities of this formulation and control formulations were measured at a variety of rates of shear (RPM) at a constant temperature of 25° C. The results of the measurements for the above formulations and the controls are graphically depicted in FIG. 7.

Figure 7:
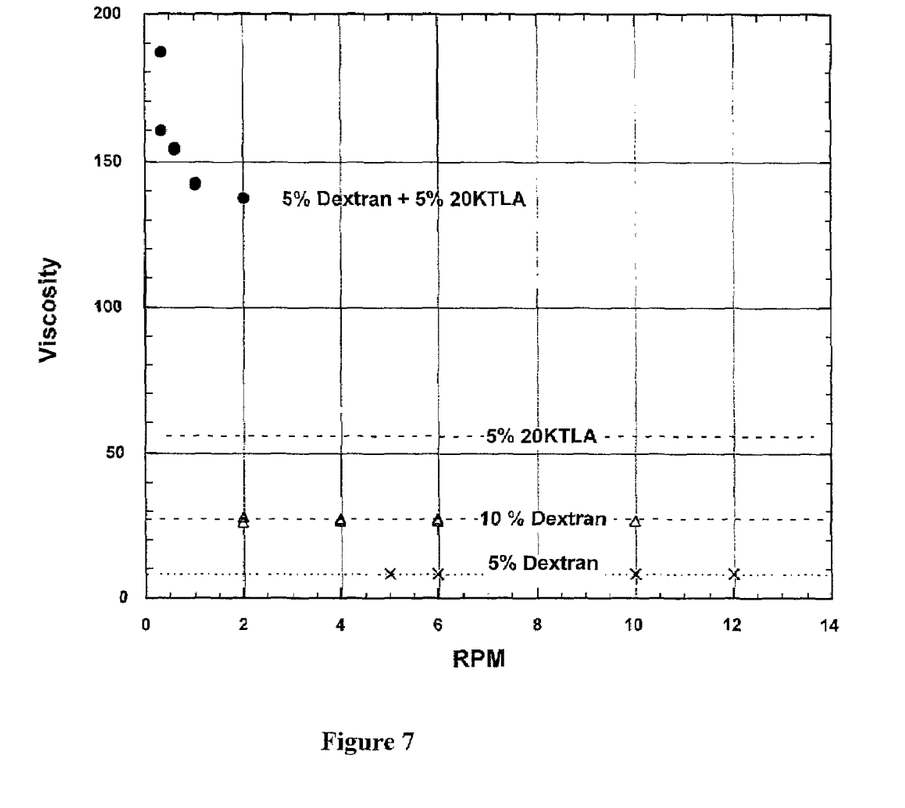
FIG. 7 is a graph of stirring rate (RPM) versus apparent viscosity (cP) at a constant temperature (25° C.) for a solution containing 5% Dextran and 5% 20KTLA and control solutions.

The 5% dextran control had a constant apparent viscosity of about 9 cP. The 10% dextran control demonstrated a constant apparent viscosity of about 27 cP. The 5% 20KTLA control solution had a constant apparent viscosity of 57 cP. In contrast, the apparent viscosity for mixture of 5% 20KTLA and 5% dextran decreased with increasing shear rate. It ranged from 187 cP (at 0.2 RPM) to 140 cP (at 2 RPM). This relationship between the viscosity and the shear stress indicates that the mixture is a pseudoplastic material.

Example 10

Effect of Change in Shear Rate on PLURONIC® F127/HA Mixture.

Figure 8:
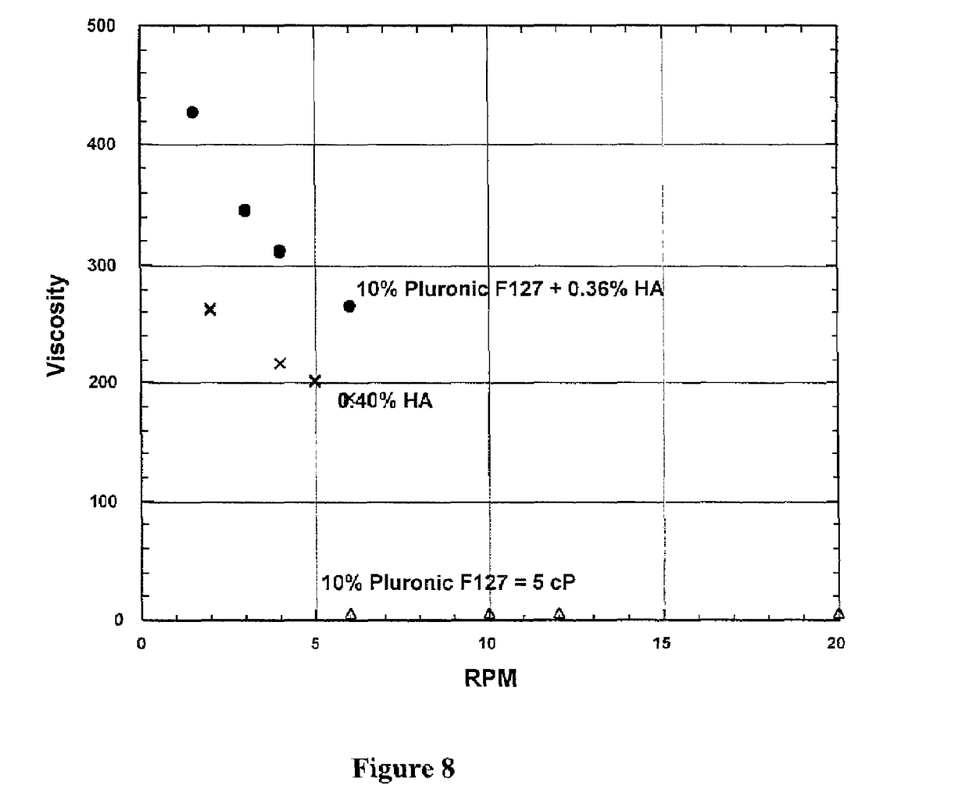
FIG. 8 is graph of stirring rate (RPM) versus apparent viscosity (cP) at constant temperature (25° C.) for a solution containing 10% PLURONIC® F-127 poloxamer and 0.36% HA and control solutions.

A 10 g aqueous formulation consisting of PLURONIC® F-127 a poloxamer (i.e. polyethylene glycol—polypropylene glycol copolymer (with a molecular weight of approximately 12.6 kDa), 36 mg HA with a molecular weight of 2000 kDa, 50 mg TEOA, 80 mg KPhos, 40 mg VC, and 0.4 mg of eosin was prepared. The apparent viscosities of this formulation and control formulations were measured at various RPM at a constant temperature of 25° C. The results of these measurements are illustrated by FIG. 8.

The viscosity for the 10% PLURONIC® F-127 control solution did not vary over increasing shear rate; it remained constant at 5 cP. The viscosity for the 0.40% HA control solution decreased with increasing shear rate. It ranged from about 285 cP (at 2 RPM) to 195 cP (at 6 RPM). The mixture of 10% PLURONIC® F-127 and 0.36% HA had a much greater apparent viscosity than its components. It ranged from about 420 cP (at 2 RPM) to about 285 cP (at 6 RPM).

Example 11

Controlled Release of Hyaluronic Acid from PAG Gels.

Solutions containing 5% low molecular weight HA (with molecular weights of 50, 150 and 500 kDa) and 8% 20KTLA were formed. The solutions were cast as discs, 4 mm thick, in a well (ca. 13 mm diameter) in a plastic plate, in a total volume of 0.5 ml, and photopolymerized with eosin. The gels were immersed in phosphate buffered saline (PBS). The concentration of HA in the supernatant was determined by chromatography.

Figure 9:
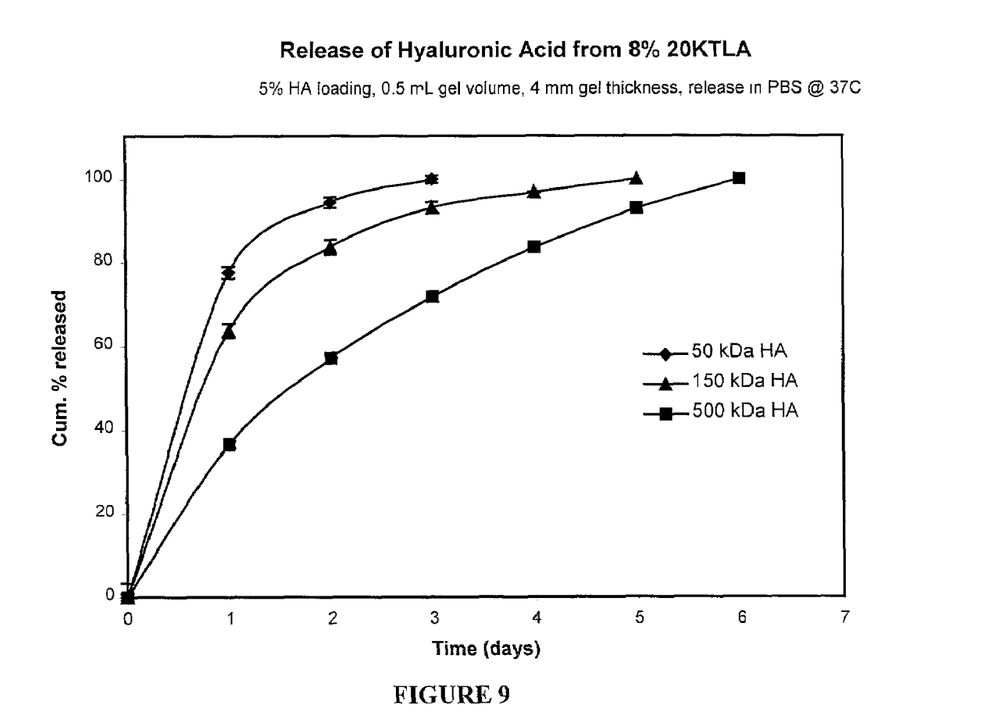
FIG. 9 is a graph of time (days) versus percent (%) HA released from three solutions with 5% HA (at molecular weights of 50 kDa, 150 kDa, and 500 kDa) and 8% 20 KTLA at a constant temperature (37° C.).

The results are shown in FIG. 9. All samples showed 100% release at about 3, 5 and 6 days respectively. The two higher concentrations demonstrated to have an increased viscosity on mixing with PAGs, as demonstrated in Table 1.

Those skilled in the art will recognize, or be able to ascertain using no more than routine experimentation, many equivalents to the specific embodiments of the invention described herein. Such equivalents are intended to be encompassed by the following claims.

We claim:

1. A polymeric composition comprising a mixture of
   a) a solution of at least one polymerizable macromer having a first viscosity, comprising at least one polyalkylene glycol (PAG) region and at least one or more chemically reactive groups which react spontaneously or under the influence of activating conditions to form polymeric structures; and
   b) a solution of at least one PAG-interacting polymer (PIP) having a second viscosity in an amount sufficient to form the mixture with a viscosity greater than the sum of the first and the second viscosities,
   wherein the composition contains between 0.05% to 20% by weight of the PIP, and between 4% to 30% weight of the polyalkylene glycol or PAG-based macromer, and
   provided that when the PIP is a hyaluronic acid, the hyaluronic acid has an average molecular weight of about 150 k Da or more.

2. The composition of claim 1, wherein the PIP is selected from the group consisting of glycosaminoglycan, cellulose, dextran, and polyvinylpyrrolidone, and salts or derivatives thereof.

3. The composition of claim 2 wherein the PIP is selected from the group consisting of hyaluronic acid, carboxymethyl cellulose, dextran, dextran sulfate, and polyvinylpyrrolidone.

4. The composition of claim 1, wherein the macromer further comprises biodegradable regions.

5. The composition of claim 1, wherein the at least one or more chemically reactive groups are selected from the group consisting of ethylenic group, acrylate group, succinimidate group, and isocyanate group.

6. The composition of claim 1, wherein the PAG-based macromer contains biodegradable linkages.

7. The composition of claim 1, wherein the PIP is hyaluronic acid and the PAG-based macromer comprises a PAG core and at least two acrylate groups.

8. The composition of claim 1, further comprises a bioactive compound, a therapeutic substance or cells.

9. A method for forming a biocompatible, flexible, bioadhesive gel comprising
  a) forming an aqueous solution comprising a mixture of
    i) at least one polymerizable macromer having a first viscosity comprising at least one polyalkylene glycol (PAG) region, and at least one or more chemically reactive groups which react spontaneously or under the influence of activating conditions to form polymeric structures; and
    ii) at least one PAG-interacting polymer (PIP) having a second viscosity in an amount sufficient to form the mixture with a viscosity greater than the sum of the first and the second viscosities,
    wherein the composition contains between 0.05% to 20% by weight of the PIP, and between 4% to 30% by weight of the polyalkylene glycol or PAG-based macromer, and
    provided that when the PIP is a hyaluronic acid, the hyaluronic acid has an average molecular weight of about 150 k Da or more;
  b) applying the solution to a surface of a substrate selected from the group consisting of cells, tissue surfaces and implants; and
  c) polymerizing the solution to form a gel.

10. The method of claim 9, wherein the solution further comprises a bioactive compound, a therapeutic substance or cells.

11. The method of claim 9, wherein the solution further comprises a therapeutic substance.

12. The method of claim 9, wherein the PIP is selected from the group consisting of glycosaminoglycan, cellulose, dextran, and polyvinylpyrrolidone, and salts or derivatives thereof.

13. The method of claim 12 wherein the PIP is selected from the group consisting of hyaluronic acid, carboxymethyl cellulose, dextran, and dextran sulfate.

14. The method of claim 9, wherein the macromer further comprises biodegradable regions.

15. The method of using the polymerizable composition of claim 1 comprising polymerizing the polymerizable composition of claim 1 to form a gel, wherein the gel is used in an application selected from the group consisting of formation of tissue coatings and tissue sealants;
  delivery of therapeutic substances; lubrication; filling voids; replacement of vitreous fluid; adherence of tissue to tissue or to a medical device; coating of a medical device; embolization; encapsulation of cells, tissues and organs; immobilization of cells, tissue and organs; treatment of the retina; treatment of joints; regeneration of a tissue; and encapsulation of medications.

16. The method of claim 15, wherein the gel is used to treat a detached retina.

17. The method of claim 11, wherein the gel is used for the local delivery of the bioactive substance to a tissue.

18. The method of claim 17, wherein the tissue is a joint.

19. The method of claim 15, wherein the gel is used to treat adhesion by application of the gel to a surface of a tissue.

20. The method of claim 15, wherein the gel is used to treat adhesion by application of the gel to a surface of an implant.

21. The method of claim 9, wherein the at least one or more chemically reactive groups are selected from the group consisting of ethylenic group, acrylate group, succinimidate group, and isocyanate group.

22. The method of claim 9, wherein the PIP is hyaluronic acid and the PAG-based macromer comprises a PAG core and at least two acrylate groups.

23. The method of claim 22, wherein step c comprises contacting the mixture to a radical initiator and then exposing the mixture to light in the UV-visible range.

* * * * *